United States Patent [19]

Niimura et al.

[11] Patent Number: 4,977,078
[45] Date of Patent: Dec. 11, 1990

[54] PLATE SUBSTRATE IMMUNOASSAY DEVICE AND METHOD FOR PERFORMING A MULTI-TEST IMMUNOASSAY ON A SPECIMEN

[75] Inventors: Toshinobu Niimura, Mineola; Tadashi Takahashi, Port Washington; Mutsuro Kashiba, Williston Park; Ko Sakai, Hew Hyde Park; Tokio Kano, Bellerose, all of N.Y.

[73] Assignee: Olympus Optical Co., Ltd., Tokyo, Japan

[21] Appl. No.: 136,822

[22] Filed: Dec. 22, 1987

[51] Int. Cl.$^5$ .................. G01N 33/53; G01N 33/48
[52] U.S. Cl. .......................... 435/7; 422/58; 422/102; 424/11; 435/810; 435/805; 436/63; 436/501; 436/518; 436/527; 436/531; 436/807; 436/809
[58] Field of Search ............ 422/58, 102, 57; 424/11; 435/7, 810, 805; 436/518, 527, 501, 531, 805, 807, 809, 823, 63

[56] References Cited

U.S. PATENT DOCUMENTS

| 4,154,795 | 5/1979 | Thorne | 422/99 |
| 4,317,810 | 3/1982 | Halbert et al. | 422/58 X |
| 4,328,183 | 5/1982 | Rosenfield | 424/11 X |
| 4,591,570 | 5/1986 | Chang | 436/518 |
| 4,599,315 | 7/1986 | Terasaki et al. | 422/102 X |
| 4,770,856 | 9/1988 | Uthemann et al. | 436/531 X |
| 4,789,628 | 12/1988 | Nayak | 435/7 |

Primary Examiner—Ester L. Kepplinger
Assistant Examiner—Carol A. Spiegel
Attorney, Agent, or Firm—Frishauf, Holtz, Goodman & Woodward

[57] ABSTRACT

An immunoassay device and a method of performing immunoassay using this immunoassay device are disclosed. The immunoassay device includes a plate substrate having a flat surface, a plurality of adjacent projections projecting on the flat surface of the plate substrate, and a plurality of immunoreaction regions formed by applying and fixing immunoassay reagents to and in flat regions defined by the adjacent projections. The immunoreaction regions are spaced apart from each other and have surface levels equal to or higher than a surface level of the plate substrate. The immunoassay device is used to simultaneously perform various types of immunoassay and requires a simple washing for immunoassay. Specimens do not flow out from the plate or mix with each other, and safe, accurate immunoassay can be performed.

11 Claims, 3 Drawing Sheets

PLATE SUBSTRATE IMMUNOASSAY DEVICE AND METHOD FOR PERFORMING A MULTI-TEST IMMUNOASSAY ON A SPECIMEN

BACKGROUND OF THE INVENTION

1. Field of the Invention

The present invention relates to a device for performing immunoassay and, more particularly, to an immunoassay device for simultaneously performing various types of immunoassay and a method of performing immunoassay using the device.

2. Description of the Prior Art

Immunoassay is a method of identifying or quantifying antigens or antibodies by utilizing high specificity and detection sensitivity in antigen-antibody reactions. In order to quickly, easily perform immunoassay, various types of devices are proposed. A simplest device is a test piece carrying one immunoassay reagent, i.e., an antibody or antigen on a strip-like support. Such a test piece performs only one type of immunoassay in each test.

In cell-typing for identifying histocompatibility, at least eighty different immunoassay tests are required. In order to simultaneously perform such a multi-test immunoassay the following conventional immunoassay device is proposed.

U.S. Pat. No. 4,591,570 describes an immunoassay device having small immunoreaction regions, i.e., small regions applied with immunoassay reagents, aligned with high density on a flat plate such as a glass or plastic cover slip. More specifically, in this device, a plurality of immunoassay reagent solutions (e.g., antibody solutions) are applied to the flat plate surface in a given sequence to form dots each having a diameter of 0.25 to 1 mm, and the immunoassay reagents are fixed by adsorption or chemical bonding to the flat plate surface. By using this immunoassay device, various immunoassay tests can be simultaneously performed.

A cell suspension as a specimen is dripped on all immunoreaction regions and different antigen-antibody reactions occur in the individual immunoreaction regions. Cell surface antigens are selectively and specifically bound with an antibody in each immunoreaction region. Therefore, by detecting the presence/absence of bonding of cells to all the immunoreaction regions and the number of cells bonded to these regions, cell-typing and a content ratio of cells to the corresponding cell suspension can be determined.

The conventional immunoassay device described above has the following disadvantages.

First, it is difficult to form small immunoreaction regions. When immunoassay reagent solutions are dripped on predetermined small regions on the flat plate surface, no marks are formed on the positions to be applied with the reagent solutions. In addition, different immunoassay reagent solutions must be applied to the predetermined areas without mixing and this operation is very difficult. It is also difficult to set the immunoreaction regions having an identical area.

Second, it is difficult to control the amount of immunoassay reagent fixed to each region on the plate surface. The amount of immunoassay reagent applied to the plate surface varies depending on the concentration of the solution applied to the plate surface, the type of reagent, and the material of the plate. In order to control the amount of immunoassay reagent, it is necessary to increase or decrease an amount of reagent solution. The reagent solution dripping on the plate surface is kept in a predetermined area of the plate surface by a surface tension. Thus, the amount of reagent solution kept in the predetermined area is limited by only the surface tension. It is, therefore, almost impossible to increase the amount of reagent solution in a predetermined area. This disadvantage also occurs in dripping of a specimen solution.

The third disadvantage is associated with a practical application to the immunoassay. Since the device has a plate with a flat surface, the specimen solution applied to the flat plate surface flows over the entire surface and may overflow. If the specimen is obtained from blood of a patient having an infectious disease, a secondary infection may be caused. When a plurality of specimens are applied to a single plate, they are mixed. Therefore, a plurality of specimens cannot be analyzed on a single plate.

A conventional example free from the above disadvantages is disclosed in U.S. Pat. No. 4,154,795. In this immunoassay device, wells having the same area are arranged in an 8×12 matrix on a surface. When this device is used, an immunoassay reagent is fixed within the inner wall surface of each well or added in it. A specimen is added to each well to cause a specific antigen-antibody reaction between the specimen and the immunoassay reagent, thereby detecting an antigen or antibody existing in the sample.

The immunoreaction region is distinctly defined by each well in the conventional immunoassay device of a well type, and the problems posed by the above conventional immunoassay devices of flat plate type can be solved. However, washing required in the immunoreaction test is very cumbersome. In order to fix an immunoassay reagent within a well region defined by the inner walls, an excess reagent must be washed after the reagent is applied to the matrix surface. A blocking agent is added to prevent nonspecific adsorption for the fixed immunoassay reagent. Washing is also required to remove any excess blocking agent and requires a cumbersome operation for supplying a washing solution (a buffer solution) into each well and removing the solution from each well, thus resulting in time-consuming operation and requiring much labor.

SUMMARY OF THE INVENTION

It is a first object of the present invention to provide an immunoassay device having various types of immunoreaction regions for simultaneously performing various types of immunoassay and the following good advantages:

(1) All immunoreaction regions are flat and allow easy washing;

(2) Each region applied with an immunoassay reagent solution or a specimen can be easily recognized when the immunoreaction region is to be formed or immunoassay is to be performed;

(3) Different immunoassay reagents or specimens are not mixed with each other;

(4) Immunoreaction regions of an identical area can be formed;

(5) When the immunoassay reagent solutions are dripped to form immunoreaction regions, the amount of reagent solution held in each predetermined region can be increased or decreased; and (6) The specimen is not flowed out of the immunoreaction region in the immunoassay test.

It is a second object of the present invention to provide a method of performing immunoassay by using the above immunoassay device.

In order to achieve the first object of the present invention, there is provided an immunoassay device comprising:

a plate substrate having a flat surface;

a plurality of projections projecting on the flat surface of the plate substrate and adjacent to each other; and a plurality of immunoreaction regions formed by applying and fixing immunoassay reagents to and in flat regions defined by the adjacent projections, the immunoreaction regions being separated from each other and having surface levels equal to or higher than a surface level of the plate substrate.

In order to achieve the second object of the present invention, there is provided a method of performing immunoassay, comprising the steps of:

preparing the above immunoassay device;

applying and holding a predetermined amount of a cell suspension serving as a specimen to and on the immunoreaction regions and side surfaces of the projections defining the immunoreaction regions and bringing the specimen into contact with the immunoreaction regions;

causing the immunoassay reagents fixed in the immunoreaction regions to react with the specimen, thereby binding cells with the immunoreaction regions;

washing unbound cells; and examining cells bound with corresponding ones of the immunoreaction regions.

In the above method, the immunoreaction regions with which the cell is bound are discriminated to qualitatively determine the presence of a specific antigen on surfaces of the the specimen cells.

The cells bound with the corresponding immunoreaction regions are quantitatively measured to determine the content ratio of cells having the specific antigen.

In the immunoassay device according to the present invention, the immunoreaction regions are not constituted by wells and have a level equal to or higher than the surface level of the plate substrate. Therefore, washing required for immunoassay can be greatly simplified.

When the immunoassay reagent solutions are dripped in predetermined regions to form the immunoreaction regions or the specimen is dripped in the immunoreaction regions in the test, the dripping positions can be accurately identified by the projections.

The dripped reagent solutions are also held by the side surfaces of the projections formed on the surface of the plate substrate, and a higher holding force can be obtained. Therefor, the reagent solution is not flowed outside the predetermined flat region. When different reagent solutions or specimen solutions are dripped in the adjacent regions, they are not mixed with each other. An increase or decrease in reagent solution or specimen held in the predetermined flat region can be achieved, and immunoreaction regions of an identical area can be formed. In addition, the specimen flow outside the immunoreaction region can be prevented to decrease the possibility for secondary infection when blood of a patient having an infectious disease is tested.

DETAILED DESCRIPTION OF THE PREFERRED EMBODIMENTS

The present invention will be described in detail with reference to the accompanying drawings.

An immunoassay device according to an embodiment will be described with reference to FIGS. 1A to 1C.

Figure 1A:
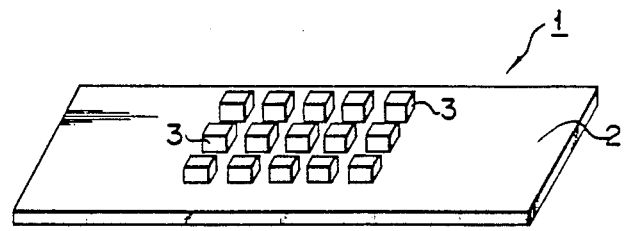
FIGS. 1A to 1C are views for explaining an embodiment of an immunoassay device according to the present invention.

Support 1 shown in FIG. 1A is used in the fabrication of this device. Support 1 comprises plate substrate 2 and small rectangular cubical projections 3 formed on substrate 2. Fifteen projections 3 are formed integrally with plate substrate 2. As shown in FIG. 1A, a $3 \times 5$ matrix is formed. Support 1 is made of a material for receiving and holding an immunoassay reagent of an antibody or antigen. Such a material is glass or plastic.

Figure 1B:
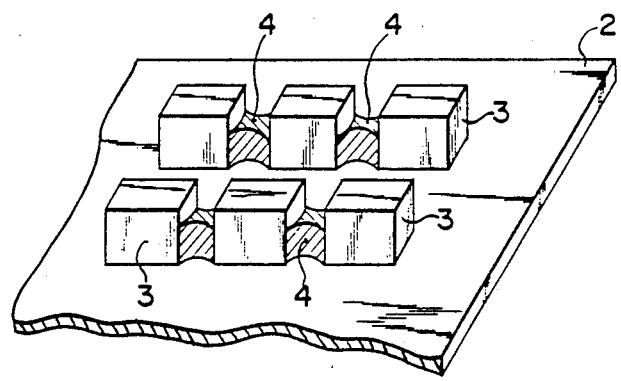

In order to fabricate the immunoassay device by using support 1, immunoassay reagent solution 4 is dripped in and applied to portions between row projections 3, as shown in FIG. 1B. Solution 4 is also attached to and held by side walls of projections 3 in addition to the surface portions of plate substrate 2. In order to effectively hold solution 4, a distance between adjacent row projections 3 is preferably 1 to 3 mm. In order to prevent adjacent solutions 4 from mixing, a distance between adjacent column projections 3 is preferably 1 to 10 mm. The appropriate height of projection 3 is 1 to 5 mm.

The immunoassay reagent solutions are applied to and fixed in the predetermined regions on the plate substrate as described above. The solutions are incubated within a predetermined period of time. The incubated solutions are washed with a buffer solution such as phosphate-buffered saline (PBS) to remove any excess immunoassay reagents. Since projections 3 . . . are aligned in a matrix shape, washing can be easily performed. In order to prevent nonspecific adsorption, the washed substrate is treated with a blocking solution. A solution of protein such as bovine serum albumin, ovalbumin, or gelatin is applied and fixed in the same manner as in FIG. 1B. The resultant substrate is then washed to remove the excess blocking agent and is dried. An immunoassay device having immunoreaction regions 5a to 5d, 6a to 6d, and 7a to 7d is prepared, as shown in FIG. 1C.

In order to perform immunoassay using the immunoassay device shown in FIG. 1C, the specimen is poured into immunoreaction regions 5a to 5d, 6a to 6d, and 7a to 7d, as described with reference to FIG. 1B. An antigen-antibody reaction occurs between the specimen and the immunoassay reagents. Of the components of the specimen, components specifically reacting with the immunoassay regent are bonded to the immunoreaction regions. The nonreacted components are washed with a proper buffer solution, and the components left in the immunoreaction regions are analyzed to perform immunoassay. An pseudo reaction region in which immunoassay reagent is not fixed can be also useful. In this case, pseudo reaction regions are formed by only a blocking treatment to determine whether the blocking treatment can be correctly performed and the number of cells adhered to the pseudo reaction region by nonspecific adsorption. A specimen as in the one used above is poured also in the pseudo reaction region, and correct washing can be performed if the specimen components are not left in the region.

The types of immunoassay reagent fixed in immunoreaction regions 5a to 5d, 6a to 6d, and 7a to 7d are decided according to immunoassay purposes.

In cell-typing, an antibody required for cell-typing is fixed in immunoreaction regions 5a to 5d, 6a to 6d and 7a to 7d as an immunoreaction reagent. In this case each immunoreaction region has a different antibody. A cell suspension of the specimen is dripped to cause a reaction between the antibody and the antigen existing on the surfaces of the cells. After the above reaction, the substrate is washed and the cells attached to each reaction region are identified visually or with a microscope. The cells may be stained as needed, for more accurate identification.

The immunoassay device shown in FIG. 1C can be used in the following application. One type of antibody is fixed in the immunoreaction regions of each column (i.e., 5a to 7a, 5b to 7b, 5c to 7c, or 5d to 7d). In this case, immunoreaction regions in the same column have the same antibody, and the regions in a different column have a different antibody. Specimen A is applied to immunoreaction regions 5a to 5d, specimen B is applied to immunoreaction regions 6a to 6d, and specimen C is applied to immunoreaction regions 7a to 7d. Four test items for three specimens A, B, and C can then be simultaneously checked. In this case, if one type of specimen is applied to the immunoreaction regions of all rows (5a to 5d, 6a to 6d, and 7a to 7d), same 4 items for one type of specimen can be checked as if it were repeated three times, thus confirming the test result.

Figure 2:
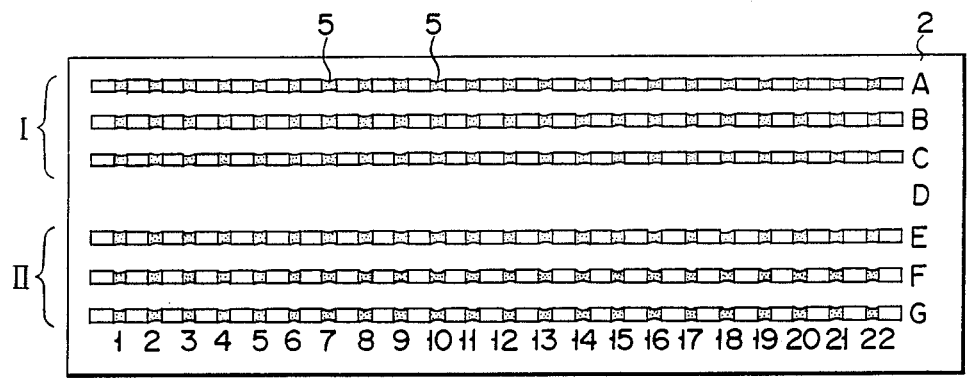
FIG. 2 is a plan view for explaining another embodiment of an immunoassay device according to the present invention.

If the number of projections 3 is increased and thus the number of immunoreaction regions is increased, the number of items to be simultaneously tested, the number of specimens to be tested, and the number of test cycles can be increased, as will be shown in FIG. 2.

FIG. 2 shows a matrix having 23×6 small projections 3. Projections 3 are divided into 23 (columns)×3 (rows) matrices I and II. An isolation band without small projections is formed between matrices I and II. Immunoreaction regions 5 in this embodiment constitute 22×3 matrices I and II.

In order to specify each immunoreaction region 5 in the embodiment of FIG. 2, letters (A to C in matrix I, E to G in matrix II, and D in the isolation band) are affixed to the rows, respectively. Numbers 1 to 22 are affixed to the columns, respectively. Therefore, each immunoreaction region can be specified by a combination of one letter and one number.

In the embodiments of FIGS. 1 and 2, projections 3 are cubical projections. However, the shape of projection 3 can be appropriately changed, as shown in FIGS. 3A to 7C.

Figure 3A:
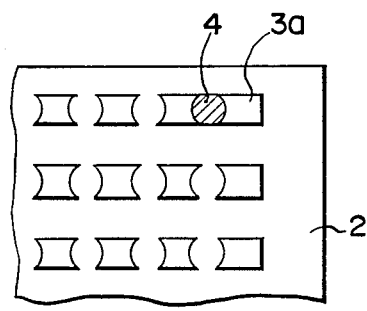
FIGS. 3A to 7C are views for explaining other embodiments of immunoassay devices according to the present invention.
Figure 3B:
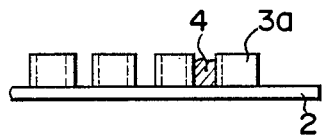

Each small projection 3a shown in FIGS. 3A and 3B has concave side surfaces applied with an immunoassay reagent solution or specimen solution 4. FIG. 3A is a plan view of the immunoassay device and FIG. 3B is a front view of the device. According to this embodiment, the holding property of the immunoassay reagent solution or specimen can be improved, and the amount of dripping can be increased. Since the shape of each immunoreaction region can be substantially circular, it matches with the field of view (circular) of a microscope and facilitates observation with the microscope.

Figure 4A:
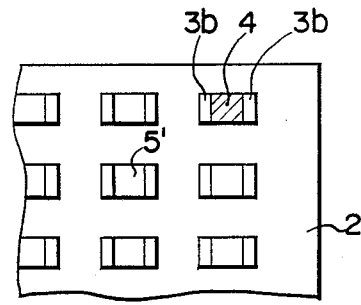
Figure 4B:
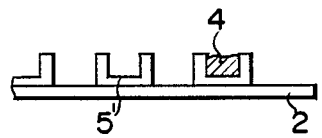

In an immunoassay device shown in FIGS. 4A and 4B, each portion 5' defined by a pair of small projections 3b and serving as an immunoreaction region has a level higher than the surface level of plate substrate 2. In this embodiment, the immunoreaction region can be clearly distinguished from nonimmunoreaction region, and immunoreaction regions of an identical area can be provided. Unlike in the well type immunoreaction region, easy washing can be advantageously facilitated.

Figure 5A:
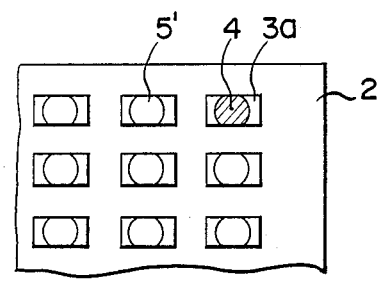
Figure 5B:
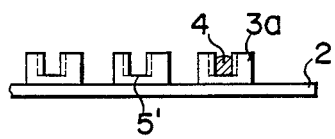

An embodiment shown in FIGS. 5A and 5B has both advantages of the immunoassay devices shown in FIGS. 3A and 3B and FIGS. 4A and 4B.

Figure 6:
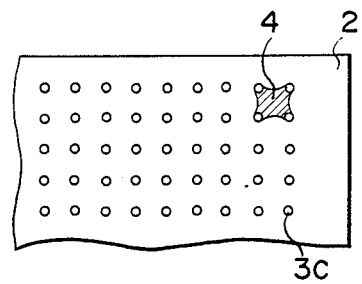

An embodiment in FIG. 6 has thin rod-line projections 3c. In this case, small projections 3c must be formed at four corners of the immunoreaction region.

Figure 7A:
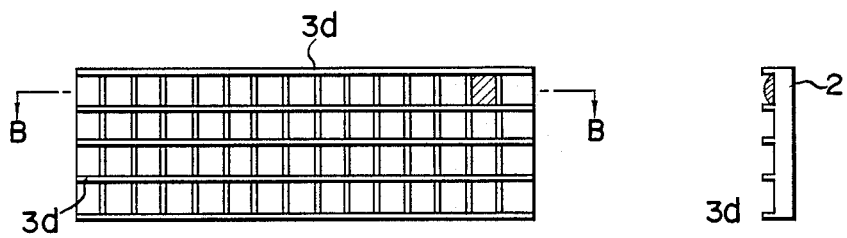
Figure 7C:
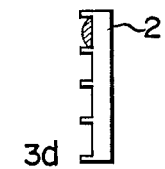
Figure 7B:
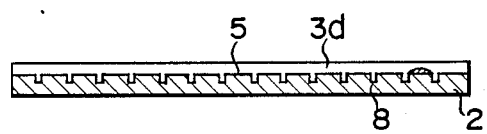

FIGS. 7A, 7B, and 7C show an embodiment as a high-density immunoreaction region structure. FIG. 7A is a plan view of the immunoassay device, FIG. 7B is a sectional view of the device taken along the line B—B of FIG. 7A, and FIG. 7C is a right side view of the device. As shown in FIGS. 7A to 7C, projections 3d each with a vertical wall and grooves 7 perpendicular to projections 3d are formed in this embodiment. Projections 3d and grooves 8 define immunoreaction regions 5. The level of immunoreaction regions 5 is higher than the level of a region (groove 8) for separating immunoreaction regions 5 in the same manner as in the embodiment of FIGS. 4A and 4B.

The present invention will be described in detail by way of its examples.

EXAMPLE 1

(Measurement of T4/T8 Ratio)

A ratio of T4 cells to T8 cells is measured by immunoassay in order to diagnose a T-cellular disease (e.g. acquired immune deficiency syndrome; to be referred to as an AIDS hereinafter). The T4 cell is a general term for cells having a cell surface antigen T4 such as a helper T cell, and the T8 cell is a general term for cells having a cell surface antigen T8 such as a suppressor T cell. It is known that the T4/T8 ratio is very low in an AIDS patient.

Figure 1C:
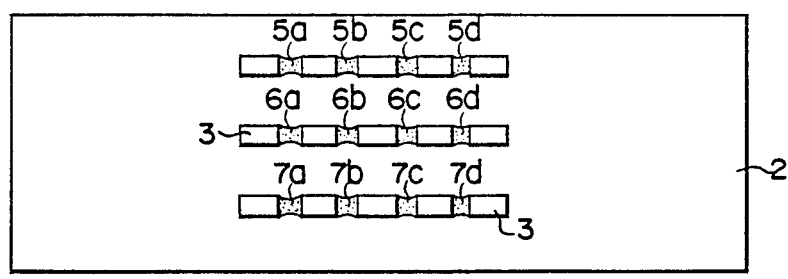

In Example 1, an immunoassay device described with reference to FIGS. 1A–1C is used. An anti-T4 monoclonal antibody is fixed in immunoreaction regions 5a, 5c, 6a, 6c, 7a, and 7c and an anti-T8 monoclonal antibody is fixed in immunoreaction regions 5b, 5d, 6b, 6d, 7b, and 7d in the following manner.

Support 1 was sufficiently washed, sterilized, and dried. The anti-T4 monoclonal antibody was poured into immunoreaction regions 5a, 5c, 6a, 6c, 7a, and 7c, and the anti-T8 monoclonal antibody was poured into immunoreaction regions 5b, 5d, 6b, 6d, 7b, and 7d. The amount of each antibody was 5 μl. Support 1 with these antibodies was left to stand in a humid room at room temperature for 2 hours. Support 1 was dipped in the PBS and dried. Dried support 1 was dipped in a 3% gelatin and was left to stand at room temperature for an hour. After the gelatin was removed from support 1, support 1 was dipped in the PBS and washed. The Washed support was dried with air to obtain an AIDS diagnostic immunoassay device.

The T4/T8 ratio measurement can be performed by using the resultant immunoassay device in the following manner.

Immunoassay is performed for six specimens A to F. Specimens A to F are human lymphocyte suspension and are poured in adjacent T4 and T8 immunoreaction regions. The amount of specimen poured in each region is 5 μl. Specimen A is poured in immunoreaction regions 5a and 5b; specimen B, to regions 5c and 5d; specimen C, to regions 6a and 6b; specimen D, to regions 6c and 6d; specimen E, to regions 7a and 7b; and specimen F, to regions 7c and 7d. These specimens are left to stand in a humid room at room temperature for 30 minutes and specific antigen-antibody reactions in the respective immunoreaction regions are performed. The immunoassay device is dipped and washed in the PBS, and cells which are not bound with the immunoreaction regions are washed. The numbers of cells bound with the T4 and T8 immunoreaction regions are measured for all specimens A to F, and T4/T8 ratios of specimens A to F are calculated.

Simultaneous measurement of the six specimens can be performed in Example 1, and the treatment capacity can be increased. Since the specimens of the AIDS patients are not flowed out of the immunoassay device, safety of the operator can be assured. In addition, the immunoassay reagents and the specimens are not mixed with each other, and accurate immunoassay can be achieved.

EXAMPLE 2

(Measurement of T/B Ratio)

A ratio of T cells to B cells (i.e., a T/B ratio) is measured. The normal T/B ratio is predetermined (i.e., a normal value). If a calculated T/B ratio is greatly deviated from the normal value, it is a suspected case of a blood disease. If the T/B ratio is large, an ATL (Adult T-cell Leukemia) is suspected since the T cells are abnormally increased in the ATL. However, if the T/B ratio is small, a B-cell cancer is suspected.

In Example 2, an immunoassay device described with reference to FIG. 1 is used. An anti-T cell antibody is fixed in immunoreaction regions 5a, 5c, 6a, 6c, 7a, and 7c, and an anti-B cell antibody is fixed in immunoreaction regions 5b, 5d, 6b, 6d, 7b, and 7d in the following manner.

Support 1 was sufficiently washed, sterilized, and dried. The anti-T cell antibody was poured into immunoreaction regions 5a, 5c, 6a, 6c, 7a, and 7c, and the anti-B cell antibody was poured into immunoreaction regions 5b, 5d, 6b, 6d, 7b, and 7d. The amount of each antibody was 5 μl. Support 1 with these antibodies was left to stand in a humid room for 2 hours. Support 1 was dipped in the PBS and dried. Dried support 1 was dipped in a 3% gelatin and left to stand at room temperature for an hour. After the gelatin was removed from support 1, support 1 was dipped in the PBS and washed. Washed support 1 was dried with air to obtain a T/B ratio measuring immunoassay device.

Immunoassay is performed for six specimens A to F. Specimens A to F are human lymphocyte suspension and are poured in adjacent T4 and T8 immunoreaction regions. The amount of specimen poured in each region is 5 μl. Specimen A is poured in immunoreaction regions 5a and 5b; specimen B, to regions 5c and 5d; specimen C, to regions 6a and 6b; specimen D, to regions 6c and 6d; specimen E, to regions 7a and 7b; and specimen F, to regions 7c and 7d. These specimens are left to stand in a humid room at room temperature for 30 minutes and specific antigen-antibody reactions in the respective immunoreaction regions are performed. The immunoassay device is dipped and washed in the PBS, and cells which are not bonded to the immunoreaction regions are washed. The support is dipped in a 5% formaldehyde solution and is incubated at room temperature for 30 minutes to fix the cells. The support is dipped in the PBS and is dried with air. The cells may be stained with fluorescein isothiocyanate (0.05 mg/ml in the PBS) at room temperature for 30 minutes after fixation with formaldehyde, as needed. The stained cells are washed with the PBS and dried with air. The number of cells bound with the T cell immunoreaction regions and B cell immunoreaction regions are counted for specimens A to F with a microscope. The number of cells per unit area is counted to calculate T/B ratios of the respective specimens.

In Example 2, the six specimens can be simultaneously tested in the same manner as in Example 1, and the treatment capacity can be increased. The specimens are not flowed outside the immunoassay device, and testing safety can be improved. The immunoassay reagents or the specimens are not mixed with each other and accurate immunoassay can be performed.

EXAMPLE 3

(HLA-Typing)

Typing of HLA (Human Leucocyte Antigen) is performed using an immunoassay device shown in FIG. 2. The type of HLA has a strong correlation with several types of diseases. By diagnosing the HLA types of the patients, susceptibility to specific diseases can be determined. This technique is promising in the field of preventive medicine. The HLA strongly influences the success or failure of organ transplantation. Therefore, HLA-typing is very significant in the field of organ transplantation.

In Example 3, immunoreaction regions I in FIG. 2 are defined as HLA detecting regions belonging to MHC class I (Major Histocompatibility Antigen Class I), and immunoreaction regions II are defined as HLA detecting regions belonging to MHC class II.

In order to perform immunoassay for HLA-A, HLA-B, and HLA-C belonging to MHC class I, immunoreaction regions of rows A, B, and C shown in FIG. 2 are used, respectively. In order to perform immunoassay for HLA-DR, HLA-DQ, and HLA-DP belonging to MHC class II, immunoreaction regions of rows E, F, and G in FIG. 2 are used, respectively.

Anti-HLA monoclonal antibodies subjected to specific reactions with the HLA, that is, A2, A3, A9, A10, A29, and A32+A25 are fixed from the left to right immunoreaction regions of row A in FIG. 2. Anti-HLA monoclonal antibodies subjected to specific reactions with the HLA, that is, B7, B8, B13, B14+B18, B27, B40+B7, BW4, and BW6 are fixed from the left to right immunoreaction regions of row B. Anti-sera for CW1, CW2, CW3, CW4, CW5, CW6, CW7, and CW8 are fixed from the left to right immunoreaction regions of row C. Anti-HLA monoclonal antibodies for DR1, DR2, DR3, DR4, DR5, DR7, DR2+DR4+DRW6, DR4+DR7, DRW6+DRW8, and DRW8+DRW12 are fixed from the left to right immunoreaction regions of row E. Anti-HLA monoclonal antibodies for DQW1, DQW3, DQWa, and the like are fixed from the left to right immunoreaction regions of row F.

The fabrication of the immunoassay device and HLA-typing using this immunoassay device will be described.

Support 1 is sufficiently washed, sterilized, and dried. The antibodies for identifying the HLA antigens described above are poured in the corresponding immunoreaction regions. The amount of each antibody poured in each immunoreaction region is 1 μl. Support 1 is left to stand in a humid room at room temperature for 2 hours. Support 1 is then dipped and washed in the PBS, dipped in a 3% gelatin, and left to stand at room temperature for an hour. After the gelatin is removed from support 1, support 1 is dipped and washed in the PBS and is dried with air, thereby preparing the HLA-typing immunoassay device.

HLA-typing can be performed using the resultant immunoassay device as follows.

Immunoassay is performed using human lymphocyte suspensions. These specimens are poured in amounts of 5 μl each in all the immunoreaction regions and are left to stand in the humid room at room temperature for 30 minutes. Specific antigen-antibody reactions in the respective immunoreaction regions are performed. The immunoassay device is dipped and washed in the PBS to wash off the cells which are not specifically reacted with the immunoreaction regions. The immunoreaction regions the cells adhered to are observed with a naked eye, a microscope, or a photoelectric detector, thereby performing HLA-typing.

According to Example 3, all required immunoassay tests for HLA-typing of the patients can be performed by a single immunoassay device, and the treatment capacity can be increased. The amount of antibody applied to each immunoreaction region can be small (1 μl), and expensive antibodies can be saved, thus decreasing the test cost. The specimen having unknown contents cannot be flowed outside the immunoassay device, and test safety can be improved. The immunoassay reagents or the specimens are not mixed with each other, and accurate HLA-typing can be performed.

According to the present invention as described above in detail, different types of immunoassay can be simultaneously performed by a single immunoassay device, and immunoassay operations are simple. The specimens are not flowed outside the plate and not mixed with each other. Therefore, many advantages such as safe and accurate immunoassay can be obtained.

What is claimed is:

1. An immunoassay device, comprising:
   a plate substrate having a flat surface; a plurality of adjacent projections projecting from the flat surface of the plate substrate with side walls of adjacent projections facing one another and defining a plurality of flat immunoreaction regions between the projections, said projections being separated and surrounding only parts of the immunoreaction regions, and said immunoreaction regions being separated and spaced apart at intervals from one another on said flat surface; and
   said plurality of flat immunoreaction regions having immunoassay reagents fixed in said regions;
   said projections being arranged on the flat surface of the plate substrate at such intervals that specimens applied to the immunoreaction regions are supported by adhering to the side walls of the projections.

2. A device according to claim 1, wherein the immunoreaction regions are arranged in a matrix form.

3. A device according to claim 2, wherein marks are affixed to rows and columns of the matrix form in order to specify the immunoreaction regions arranged in the matrix form.

4. A device according to claim 1, wherein the immunoreaction regions are divided into a plurality of groups, the immunoreaction regions of the respective groups constitute matrices, and spaces between the matrices are wider than spaces between the immunoreaction regions to form an isolation band.

5. A device according to claim 1, wherein the projections are cubical projections.

6. A device according to claim 1, wherein the side surfaces of the opposite projections defining each immunoreaction region therebetween constitute concave surfaces.

7. A device according to claim 1, wherein the surface level of the immunoreaction regions is the same level as that of the plate substrate.

8. A device according to claim 1, wherein the surface level of the immunoreaction regions is higher than the surface level of the plate substrate.

9. An immunoassay method for detecting cells with specific cell surface antigens, comprising the steps of:
   preparing an immunoassay device having a plate substrate with a flat surface, forming a plurality of adjacent projections projecting from the flat surface of the plate substrate with side walls of adjacent projections facing one another, defining a plurality of flat immunoreaction regions between said projections by fixing immunoassay reagents corresponding to the specific cell surface antigens in the flat regions defined by the adjacent projections, said projections being separated and surrounding only parts of the immunoreaction regions such that specimens applied to the immunoreaction regions are supported by adhering to the side walls of the projections and said immunoreaction regions being separated and spaced apart at intervals;
   applying a predetermined amount of a cell suspension specimen to the immunoreaction regions;
   reacting the specimen with the immunoassay reagents fixed in the immunoreaction regions;
   washing away unbound cells; and
   checking the immunoreaction regions for bound cells to qualitatively determining the presence of cells with the specific cell surface antigens.

10. A method according to claim 9, wherein cells with HLA-antigens are detected.

11. An immunoassay method for determining a ratio of cells with specific cell surface antigens, comprising the steps of:
   preparing an immunoassay device having a plate substrate with a flat surface, forming a plurality of adjacent projections projecting from the flat surface of the plate substrate with side walls of adjacent projections facing one another, defining a plurality of flat immunoreaction regions between said projections by fixing immunoassay reagents corresponding to the specific cell surface antigens in the flat regions defined by the adjacent projections, said projections being separated and surrounding only parts of the immunoreaction regions such that specimens applied to the immunoreaction regions are supported by adhering to the side walls of the projections and said immunoreaction regions being separated and spaced apart at intervals;
   applying a predetermined amount of a cell suspension specimen to the immunoreaction regions;
   reacting the specimen with the immunoassay reagents fixed in the immunoreaction regions;
   washing away unbound cells; and
   counting and comparing the number of the cells bound to the specific immunoreaction regions and determining the ratio of cells having the specific antigens.

* * * * *